United States Patent [19]

Muir et al.

[11] Patent Number: 5,684,101
[45] Date of Patent: Nov. 4, 1997

[54] FREE RADICAL POLYMERISATION PROCESS

[75] Inventors: Andrew Victor Graham Muir, Guildford; John Robert Lawson, Middleton; David Mark Haddleton, Kenilworth, all of United Kingdom

[73] Assignee: Zeneca Limited, London, England

[21] Appl. No.: 727,659

[22] PCT Filed: Mar. 17, 1995

[86] PCT No.: PCT/GB95/00577

§ 371 Date: Oct. 11, 1996

§ 102(e) Date: Oct. 11, 1996

[87] PCT Pub. No.: WO95/27737

PCT Pub. Date: Oct. 19, 1995

[30] Foreign Application Priority Data

Apr. 11, 1994 [GB] United Kingdom .................. 9407129

[51] Int. Cl.[6] .................................................. C08F 4/12
[52] U.S. Cl. ..................................... 526/172; 526/94
[58] Field of Search ................................. 526/172, 94

[56] References Cited

U.S. PATENT DOCUMENTS

| | | |
|---|---|---|
| 4,526,945 | 7/1985 | Carlson et al. |
| 4,680,352 | 7/1987 | Janowicz et al. ........................ 526/172 |
| 4,680,354 | 7/1987 | Lin et al. ................................ 526/172 |
| 5,602,220 | 2/1997 | Haddleton et al. ...................... 526/172 |

FOREIGN PATENT DOCUMENTS

| | | | |
|---|---|---|---|
| 0 196 783 | 10/1986 | European Pat. Off. | C08F 2/38 |
| 199 436 | 10/1986 | European Pat. Off. | |
| WO 87/03605 | 6/1987 | WIPO | C08F 4/39 |

OTHER PUBLICATIONS

N.S. Enikolopyan et al, J. Polym. Sc. Polymer Chem Ed., vol. 19, 879 (1981).

Primary Examiner—Joseph L. Schofer
Assistant Examiner—N. Sarofim
Attorney, Agent, or Firm—Cushman Darby & Cushman IP Group Pillsbury Madison & Sutro LLP

[57] ABSTRACT

Process for the free-radical polymerization of at least one olefinically unsaturated monomer, the polymerization being performed in the presence of a compound for effecting molecular weight control, being a CoII chelate of the following formula:

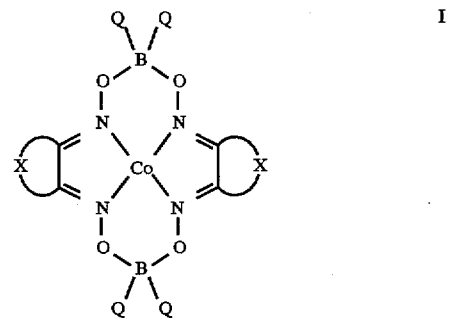

wherein each group X is a divalent group which forms with the two carbon atoms to which it is bonded a pericondensed polycyclic group, being a group having 3 or more carbocyclic rings where the oxime-containing carbocyclic ring has carbon atoms in common with 2 or more of the other rings, the polycyclic group being unsubstituted (apart from the oxime groups) or having at least one hydrocarbyl substituent; and wherein each group Q is independently selected from F, Cl, Br, OH, $C_{1-12}$ alkoxy, aryloxy, $C_{1-12}$ alkyl and aryl; or two Q groups taken together provide on one or both boron atoms a group —O—(G)—O— where G is a divalent aryl or alicyclic linking group or an alkylene linking group; or two Q groups taken together on one or both boron atoms provide a 1,5-cyclooctanediyl linking group; or being a CoIII analogue of the cobalt II chelate in which the Co atom is additionally covalently bonded to H, a halide or other anion, or a homolytically dissociable organic group. Novel Co chelates for use in the process are also disclosed.

23 Claims, No Drawings

FREE RADICAL POLYMERISATION PROCESS

This application is the national phase of international application PCT/GB95/00577, filed Mar. 17, 1995.

The present invention relates to a process for the free-radical initiated polymerisation of olefinically unsaturated monomer(s) in which molecular weight control is achieved by the presence of certain cobalt chelate complexes.

Polymers of low molecular weight, known as oligomers, are often desired for various applications (such as coating compositions) either in their own right or as precursors for other polymers. In order to form oligomers it is necessary to appropriately control the polymerisation process being used to yield the desired type of product. In free-radical polymerisations, which are widely used for polymerising olefinically unsaturated monomers, various conventional means are employed for controlling and limiting the molecular weight of the growing polymer chains. Of these, the addition of thiol compounds to the polymerisation has probably bean used the most extensively; the thiol acts as an effective chain transfer agent but unfortunately contaminates the system to which it has been added by virtue of its distinctive and persistent odour.

More recently, attention has turned to the use of various transition metal complexes, particularly cobalt chelate complexes, as chain transfer agents for use in controlling molecular weight when radically polymerising olefinically unsaturated monomers.

For example, various literature references, such as N. S. Enikolopyan et al, J. Polym. Sci., Polym. Chem. Ed., Vol 19, 879 (1981), disclose the use of cobalt II porphyrin complexes as chain transfer agents in free radical polymerisation, while U.S. Pat. No. 4,526,945 discloses the use of dioxime complexes of cobalt II for such a purpose. Various other publications, e.g. U.S. Pat. No. 4,680,354, EP-A-0196783, and EP-A-0199436, describe the use of certain other types of cobalt II chelates as chain transfer agents for the production of oligomers of olefinically unsaturated monomers by free-radical polymerisation. WO-A-87/03605 on the other hand claims the use of certain cobalt III chelate complexes for such a purpose.

We have now discovered that molecular weight control in the free-radical polymerisation of olefinically unsaturated monomers may be very effectively achieved with a further class of cobalt chelate complexes which have not been disclosed in the prior art.

According to the present invention there is provided a process for the free-radical polymerisation of olefinically unsaturated monomer(s) (especially methacrylic monomer (s)) using a free-radical initiator, the polymerisation being performed in the presence of a compound for effecting molecule weight control, the molecular weight control compound being a CoII chelate of the following formula I:

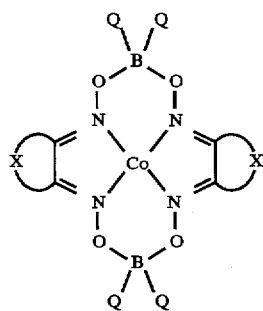

wherein each group X is a divalent group which forms with the two carbon atoms to which it is bonded a pericondensed polycyclic group, this being a group having 3 or more carbocylic rings where the oxime-containing carbocyclic ring has carbon atoms in common with 2 or more of the other rings, said polycyclic group preferably having at least one aromatic ring, and said polycyclic group being unsubstituted (apart from the oxime groups) or having at least one hydrocarbyl substituent; and wherein each group Q is independently selected from F, Cl, Br, OH, $C_{1-12}$ alkoxy, aryloxy (preferably $C_{6-10}$, more preferably phenoxy), $C_{1-12}$ alkyl and aryl (preferably $C_{6-10}$, more preferably phenyl); or two Q groups taken together provide on one or both boron atoms a group —O—(G)—O— where G is a divalent aryl or alicyclic linking group or an alkylene linking group; or two Q groups taken together on one or both boron atoms provide a 1,5-cyclooctanediyl linking group; or being a CoIII analogue of said cobalt II chelate of formula I in which the Co atom is additionally covalently bonded, usually in a direction at right angles to the macrocyclic chelate ring system, to H, halide or other anion, or a homolytically dissociable organic group.

As recited above, by a pericondensed polycyclic group in this specification is meant a group having 3 or more carbocyclic rings (including the oxime-containing ring), i.e. the ring atoms being only of carbon atoms, where the oxime-containing carbocyclic ring has carbon atoms (not necessarily the same carbon atoms of course) in common with 2 or more of the other rings (usually 2 or 3 of the other rings) of the polycyclic group.

For example, the oxime-substituted ring may have two pairs of adjacent carbon atoms, each pair being respectively shared (i.e. being in common) with two different rings of the polycyclic group as in formula IV below; note that if the group X in IV were a pyrene-derived group rather than a phenanthrene-derived group, as is possible, the oxime-substituted ring would have the second and third carbon atoms of the adjacent pairs of carbon atoms common to the additional ring of the pyrene ring system, with each of these carbon atoms being individually common to two other rings of the system (i.e. apart from the oxime ring). Also, for example, the oxime-substituted ring may have three consecutive carbon atoms in which the first and second carbon atoms are common with another ring of the polycyclic group and the second and third carbon atoms are common with a further ring of the polycyclic group, as in formula V below. Note that in this arrangement one of the carbon atoms is individually common to 3 rings of the polycyclic ring system.

The polycyclic group may in principle be wholly alicyclic in character, but more usually at least 1 of the non oxime-containing rings is aromatic in character, and more preferably at least two of the non oxime-containing rings are aromatic in character.

The carbon atoms of the polycyclic ring system are normally unsubstituted (apart from the oxime groups of course) but may optionally be substituted with a hydrocarbyl group(s) (i.e. a group(s) of only carbon and hydrogen, preferably alkyl of 1 to 12 carbons).

The two groups X are usually the same, although in principle they may be different.

The group X is in particular selected from those of the following formulae II and III

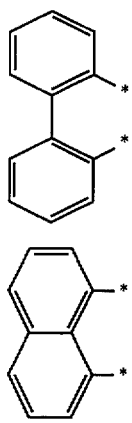

giving rise to preferred cobalt II chelates of the following formulae IV and V.

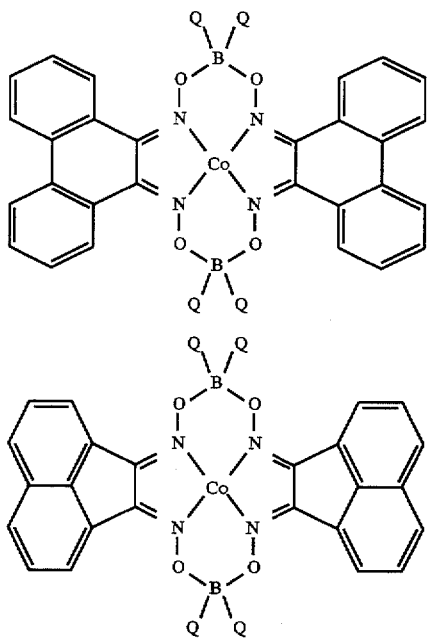

An example of a cobalt II chelate in which both the polycyclic groups X are wholly alicyclic in character is the cobalt chelate of formula IV in which the four aromatic rings shown are wholly reduced.

The groups Q are preferably all the same and more preferably are all F.

[Where both Q groups together provide a group —O—(G)—O— where G is a divalent aryl or alicyclic linking group, the group G preferably has 6 to 10 carbon atoms and linkage is from adjacent ring carbon atoms; more preferably G is o-phenylene or 1,2-cyclohexanediyl. Where G is alkylene it preferably has the formula —(CR$^1_m$)$_m$— where each R$^1$ is independently hydrogen or C$_x$H$_{2x+1}$ where x is 1 to 12 and m is 2 or 3.]

Therefore particularly preferred CoII chelates for use in the invention process are those of formula VI, which is the material having formula IV in which all the Q's are F, end formula VII, which is the material having formula V in which all the Q's are F.

The Co chelates used in the invention are electrically neutral, the surrounding ligands providing a double negative charge to balance the Co$^{2+}$ charge. The negative charges are believed to be delocalised rather than being on any particular atoms.

It is further believed that the chelate complexes defined supra are novel and inventive compounds in their own right.

There is therefore further provided according to the invention a CoII chelate complex of any formulae I to VII as defined supra and also the CoIII analogues of such complexes as defined supra.

With regard to the CoIII analogues of said compounds of said formulae, these arise when the Co is additionally bonded to a further atom, ion or organic group which is homolytically dissociable, such as H, optionally substituted alkyl (preferably C$_{1-12}$), cyano, halide, ester, aryl (preferably C$_{6-10}$) (including heterocyclic aryl, preferably C$_{6-10}$), and alicyclyl (preferably C$_{6-10}$) (including heterocyclic alicyclyl, preferably C$_{6-10}$), such a further group usually being located in an axial position (i.e. perpendicular to the equatorial ligands, the latter being as shown in the formulae above). (See e.g. WO-A-87/03605 for other compounds of a CoIII chelate type). Preferred are the analogous CoIII complexes in which the CoIII is reducible to CoII under the conditions of the polymerisation. Alkyl groups bearing one or more substituents on the carbon atom bonded to the metal ion are particularly suitable; such substituents may include nitrile, ester and optionally substituted aromatic groups. Some of these CoIII complexes may be stable materials under ordinary storage conditions, and may only react under the free-radical-generating conditions of the polymerisation process. Others, particularly where H is the further (axial) group, may be highly reactive intermediate species—and indeed it is possible that all the CoII complexes (and possibly the CoIII ones as well) exert their chain transfer effect by proceeding through the reactive CoIIIH intermediate. It is also possible that there is always a periodic interchange between the CoII and CoIII valency states in the complexes during the polymerisation. In fact the actual mechanism of involvement is complex and not properly understood on our part and we do not wish to be bound by any particular theory nor to an identification of the specific chemical constitution or valency state of the Co complex during the actual polymerisation process.

It is also possible for the cobalt complexes as defined supra (i.e. CoII or CoIII complexes) to additionally have further ligands coordinated to the Co atom (presumably axially), which do not alter the Co valency state. These may be derived en passant from the reaction medium used in the preparation of the Co complex or from the polymerisation medium used in the polymerisation process, or may be derived by deliberately adding a compound which will provide such ligands, and it is often the case that the coordinated presence thereof in the complex will ameliorate the latter's effectiveness. However, they are not essential to the invention, and for convenience they have not been shown in the various formulae. Typical of such additional ligands are weakly basic tertiary amines such as pyridine (or their substituted derivatives), trialkyl amines, dialkylamines, ethers such as tetrahydrofuran and diethyl ether, and also optionally substituted trialkyl, triaryl or tri(alkyl/aryl) phosphines (or analogous compounds such as corresponding alkoxy or aryloxy phosphines). (The alkyl groups mentioned above preferably, and independently, are of 1–14 carbons and the aryl groups are preferably, and independently, are of 6–10 carbons, more preferably phenyl). One or more water molecules could also be coordinated to the Co complex.

The defined cobalt chelate complexes allow the efficient production of oligomers and are likely to be functioning as catalytic chain transfer agents (CCTA's), and are sometime referred to as such in this specification. Generally speaking, the degree of polymerisation of such oligomers (overall in the case of copolymers) will usually be within the range 2 to about 1000 (i.e. 2 to 1000 polymerised units), preferably 2 to 500, more preferably 10 to 500, and still more preferably 10 to 150.

The polymerisation process can be carried out in the presence of a polymerisation medium (acting as a carrier medium for the components and as a heat transfer medium) or in the absence of such a medium (i.e. in bulk). When using a polymerisation medium, the polymerisation may be e.g. a solution (in organic solvent), or a suspension or emulsion (in an aqueous medium) polymerisation.

Typical organic solvents which may be used as the medium for the polymerisation include aromatic hydrocarbons such as benzene, toluene, and the xylenes; ethers such as diethyl ether, tetrahydrofuran, alkoxylated ethylene glycol or polyethyleneglycol; alcohols such as methanol, ethanol, propanol and butanol and their esters with carboxylic acids such as acetic, propionic and butyric acids, ketones such as acetone or methyl ethyl ketone; and liquid tertiary amines such as pyridine. Mixtures of solvents may be used. Water may also be used as a polymerisation medium (sometimes in combination with a solvent (s) such as described above) as in suspension or emulsion polymerisations, and for such processes conventional emulsifying or suspension agents (stabilisers) may be employed. When conducting suspension polymerisation suitable suspension agents include protective colloids such as partially hydrolysed polyvinylacetate (various degrees of hydrolysis), polyacrylic acid of varying molecular weight, cellulose derivatives, gelatin and polyvinyl pyrollidone. The amount used is usually 0.1 to 8%, calculated on monomer weight. Salts such as $Na_2SO_4$ are also often included for reducing monomer solubility in the aqueous phase and to improve stabilisation.

It is most preferred, in the invention process, to employ suspension or solution polymerisation.

The polymerisations are usually performed at a temperature within the range of 25° to 160° C. (more usually 45° to 90° C.). Any suitable free radical yielding initiator may be used in the process of the invention, the usual criteria being that it has acceptable solubility in one or more of the other polymerisation components (e.g. solvent, monomers, or water), is sufficiently active at the polymerisation temperature (usually having a half life within the range 0.5 to 5 hours), and does not unacceptably affect the stability of the Co chelate. Examples of such free-radical-yielding initiators include azo compounds as 2,2'-azobis(isobutyronitrile) (AIBN), 2,2'-azobis-(2-methyl)butanenitrile, 4,4'-azobis(4-cyanovaleric acid), 2-(t-butylazo)-2 -cyanopropane, 2,2'-azobis[2-methyl-N-(1,1)-bis(hydroxymethyl)-2-hydroxyethyl]-propionamide, and 2,2'-azobis[2-methyl-N-hydroxyethyl)]-propionamide. Other soluble free radical initiators may also be used, examples of which include peroxy compounds such as benzoyl peroxide and lauroyl peroxide. Combinations of initiators may of course be used.

The use of the defined Co chelates as molecular weight control compounds in the invention process avoids the requirement to use conventional chain transfer agents which often have disadvantages of one sort or another. For example, mercaptans impart a pronounced odour, and (unlike the defined Co chelates) cannot be used to incorporate certain monomers such as glycidyl methacrylate into the oligomers (this monomer being incompatible with thiol-containing chain transfer agent due to reaction of the epoxide ring). Halogenated hydrocarbons (such as bromoform or carbon tetrachloride), on the other hand, are environmentally suspect. α-Methyl styrene (another known chain transfer agent), possibly in combination with styrene itself, is rather more expensive than methyl methacrylate and often has to be used at very high levels, e.g. up to 35 weight % (although its deliberate use as a comonomer is not of course precluded; similarly the use of styrene itself as a comonomer is not precluded).

The defined Co chelate, acting to control molecular weight, may be used in a very low amount (because it acts in a catalytic manner) in comparison to conventional chain transfer agents for achieving comparable molecular weight reduction. This allows a much purer product to be made.

The invention process may be carried out using an "all-in-one" batch process in which all components are present in the reaction medium at the start of polymerisation or a semi batch process in which one or more the components employed (usually at least one of the monomers) is wholly or partially fed to the polymerisation medium during the polymerisation.

The chelates used in the process may be prepared beforehand or may be formed in-situ from the appropriate reactants. Typically the level of the cobalt chelate used in the polymerisation process will be such that the ratio of monomer(s)/free-radical initiator (molar basis) is within the range of from 20 to 500, more usually 40 to 300. Also typically, the level of cobalt employed will be such that the ratio of cobalt chelate to free-radical initiator (molar basis) is within the range of 0.001 to 0.1, more usually 0.003 to 0.08. Also typically, the molar ratio of monomer(s) to Co chelate will often be in the range from 5,000/1 to 2,000,000/1.

The process of the invention is most effectively applied to the homo- or copolymerisation of methacrylate esters and styrenes, although acrylate esters can be polymerised effectively if included as comonomers. The process has a particular utility in that it may be employed for the polymerisation of acid-functional monomers.

Examples of monomers that may be polymerised include methyl methacrylate, ethyl methacrylate, butyl methacrylate (all isomers), and other alkyl methacrylates (usually up to 14 carbons); corresponding acrylates; also functionalised methacrylates and acrylates including glycidyl methacrylate, trimethoxysilyl propyl methacrylate, allyl methacrylate, hydroxyethyl methacrylate, hydroxypropyl methacrylate, dialkylaminoalkyl methacrylates; fluoroalkyl (meth) acrylates; methacrylic acid, acrylic acid; fumaric acid (and esters), itaconic acid (and esters), maleic anhydride; styrene, α-methyl styrene; vinyl halides such as vinyl chloride and vinyl fluoride; acrylonitrile, methacrylonitrile; vinylidene halides of formula $CH_2=C(Hal)_2$ where each halogen is independently Cl or F; optionally substituted butadienes of the formula $CH_2=C(R^2)$ $C(R^2)=CH_2$ where $R^2$ is independently H, C1 to C10 alkyl, Cl, or F; sulphonic acids or derivatives thereof of formula $CH_2=CHSO_2OM$ wherein M is Na, K, Li, $N(R^3)_4$, H, $R^3$, or $-(CH_2)_2-D$ where each $R^3$ is independently H or C1 to C10 alkyl, D is $CO_2Z$, OH, $N(R^3)_2$ or $SO_2OZ$ and Z is H, Li, Na, K, or $N(R^3)_4$; acrylamide or derivatives thereof of formula $CH_2=CHCON(R^3)_2$, and methacrylamide or derivatives thereof of formula $CH_2=C(CH_3)CON(R^3)_2$. Mixtures of such monomers may be used.

Preferred monomers are C1–C10 alkyl methacrylates and acrylates, hydroxy C1–C14 alkyl methacylates and acrylates, such as hydroxyethyl methacrylate and hydroxypropyl methacrylate, methacrylic acid and/or acrylic acid, styrene and styrene derivatives and epoxy $C_{1-14}$ alkyl methacrylates such as glycidyl methacrylate.

The oligomers prepared by the invention process find particular utility in coatings, inks, and adhesives applications.

The present invention is now illustrated but in no way limited by reference to the following examples. Unless otherwise specified all parts, percentages and ratios are on a weight basis. The prefix C before an example denotes that it is comparative.

GENERAL PROCEDURES (i) Solution Polymerisation

To a 200 ml Schlenk tube filled with dry nitrogen and 0.085 g AIBN (2,2'-azobis(isobutyronitrile), recrystallised from ethanol) were added the appropriate amounts of the monomer(s) (typically 10 ml methyl methacrylate, MMA) and 20 ml of the appropriate solvent, all of which had been previously sparged with dry nitrogen. The desired amount of cobalt catalyst was then added and the tube heated at 60° C. under nitrogen.

(ii) Suspension Polymerisation 400 g of distilled water, 0.6 g sodium sulphate and 2.4 g HX39 stabiliser (polyacrylic acid) were degassed with nitrogen for 1 hour and charged to a reactor, heated to 80° C. and then a solution of 100 g degassed monomer(s) containing the quoted amount of AIBN and the appropriate amount of cobalt catalyst was added and the reaction stirred at 500 rpm in a reactor inside a water bath at 80° C. under nitrogen for 3 hours.

EXAMPLES 1–3, C4

Solution polymerisation of MMA in methylethyl ketone (MEK) using Co(II) (diphenanthrenequinone dioxime-diBF$_2$) as a catalytic chain transfer agent Co(II) (diphenanthrenequinone dioxime-diBF$_2$), being the complex of formula VI (i.e. the complex of formula IV in which all Q's are F with the oxime groups in the 9, 10 position), was synthesised as follows. CoII di(9,10-diphenanthrenequinone dioxime-H$_2$), i.e. the complex in which the oxime oxygens are linked to H, was synthesised from the reaction of stoichiometric equivalents of 9,10-phenanthrenequinone dioxime and cobalt acetate hexahydrate in methanol under a nitrogen atmosphere. The boron difluoride derivative was synthesised by reaction of CoII di(9,10-diphenanthrenequinone dioxime-H$_2$) with excess BF$_3$ in diethyl ether under nitrogen.

The general procedure for solution polymerisation described above was followed and the results are detailed below in Table 1. [MMA]/[Co] means the mole ratio of MMA to Co catalyst. Mw is the weight average molecular weight; Mn is the number average molecular weight.

TABLE 1

| Ex No | [MMA]/[Co]    | Mn     | Mw/Mn |
|-------|---------------|--------|-------|
| 1     | 50,000        | 626    | 2     |
| 2     | 102,400       | 655    | 2     |
| 3     | 256,400       | 1,004  | 2     |
| CR    | 0 (no Co cat) | 57,920 | 1.9   |

EXAMPLES 5–9, C10

Suspension polymerisation of MMA using Co(II) (diphenanthrenequinone dioxime-diBF$_2$) as a catalytic chain transfer agent The Co complex (of formula VI) was synthesised as described above. The general procedure for suspension polymerisation described above was followed. The results are shown in Table 2. [AIBN] means the concentration of AIBN initiator used in terms of weight % based on monomer; [Co] means the amount of Co complex using in g.

TABLE 2

| Ex No | [AIBN] (wt %) | [Co] (g) | Mn      | Mw/Mn |
|-------|---------------|----------|---------|-------|
| 5     | 1.25          | 0.025    | 3,562   | 1.8   |
| 6     | 1.25          | 0.05     | 3,902   | 1.8   |
| 7     | 1             | 0.015    | 1,677   | 2.2   |
| 8     | 1             | 0.1      | 6,265   | 2.5   |
| 9     | 1             | 0.005    | 8,793   | 2.5   |
| C10   | 1.25          | 0        | 143,500 | 3.9   |

EXAMPLES 11, 12

Suspension polymerisation of MMA and Methacrylic Acid (MAA) using CoII (diphenanthrenequinone dioxime-diBF$_2$) as a catalytic chain transfer agent The Co complex used was described above. The general procedure for suspension polymerisation described above was followed but using a mixture of MMA and MAA instead of MMA alone. The results are shown in the following Table 3. [MAA] means the % by weight of MAA based on total monomer weight. [AIBN] and [Co] have the meanings set out in Examples 5–10.

TABLE 3

| Ex No | [AIBN] (wt %) | [MAA] (wt %) | [Co] (g) | Mn    | Mw/Mn |
|-------|---------------|--------------|----------|-------|-------|
| 11    | 1             | 4            | 0.015    | 4,559 | 2.6   |
| 12    | 1             | 8            | 0.015    | 5,382 | 2.6   |

EXAMPLES 13, 14, C16

Solution polymerisation of MMA in MEK using Co (II) (diacenaphthenequinone-diBF$_2$) as a catalytic chain transfer agent The Co catalyst used in these examples was that of formula VII (i.e. the complex of formula V with all the Q's being F) and was prepared using an analogous synthetic procedure to that used for Co(diphenanthrenequinonedioxime-diBF$_2$) as described above, but starting from acenaphthenequinonedioxime.

The general procedure for solution polymerisation described above was followed. The results are shown in the following Table 4. [MMA]/[Co] has the meaning set out in Examples 1–4.

TABLE 4

| Ex No | [MMA]/[Co] | Mn     | Mw/Mn |
|-------|------------|--------|-------|
| 13    | 300,000    | 14,939 | 2.6   |
| 14    | 200,000    | 11,419 | 2.8   |
| 15    | 100,000    | 8,561  | 2.6   |
| C16   | 0          | 31,900 | 2.5   |

EXAMPLES 17, 18

Suspension polymerisation of MMA using CoII (diacenaphthenequinonedioxime-diBF$_2$) as a catalytic chain transfer agent The Co complex used was that described in Examples 13–15. The general procedure for suspension polymerisation described above was followed. The results are shown in the following Table 5. [AIBN] and [Co] have the meanings set out in Examples 5–10.

TABLE 4

| Ex No. | [AIBN] (wt %) | [Co] (g) | Mn | Mw/Mn |
|---|---|---|---|---|
| 17 | 1.25 | 0.025 | 28,000 | 2 |
| 18 | 1.25 | 0.05 | 13,320 | 2 |

The above results illustrate that the Co chelates used in the process of the invention are exceptionally effective catalyst compounds for the control and limitation of polymer molecular weight.

We claim:

1. Process for the free-radical polymerisation of at least one olefinically unsaturated monomer using a free-radical initiator, the polymerisation being performed in the presence of a compound for effecting molecular weight control, wherein the molecular weight control compound is a CoII chelate of the following formula I:

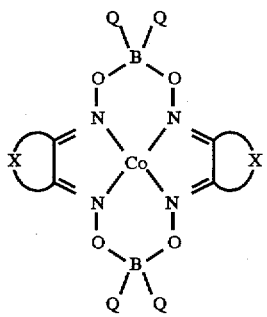

wherein each group X is a divalent group which forms with the two carbon atoms to which it is bonded a pericondensed polycyclic group, being a group having 3 or more carbocyclic rings where the oxime-containing carbocyclic ring has carbon atoms in common with 2 or more of the other rings, said polycyclic group being unsubstituted (apart from the oxime groups) or having at least one hydrocarbyl substituent; and wherein each group Q is independently selected from F, Cl, Br, OH, $C_{1-12}$ alkoxy, aryloxy, $C_{1-12}$ alkyl and aryl; or two Q groups taken together provide on one or both boron atoms a group —O—(G)—O— where G is a divalent aryl or alicyclic linking group or an alkylene linking group; or two Q groups taken together on one or both boron atoms provide a 1,5-cyclooctanediyl linking group; or being a CoIII analogue of said cobalt II chelate of formula I in which the Co atom is additionally covalently bonded to H, a halide or other anion, or a homolytically dissociable organic group.

2. Process according to claim 1 wherein said pericondensed polycyclic group has at least one aromatic ring.

3. Process according to claim 2 wherein said pericondensed polycyclic group has at least two aromatic rings.

4. Process according to any one of the preceding claims wherein said pericondensed polycyclic group has carbon atoms in common with 2 or 3 of the other rings.

5. Process according to any one of the preceding claims wherein said pericondensed polycyclic group is unsubstituted (apart from the oxime groups) or has at least one substituent which is $C_{1-12}$ alkyl.

6. Process according to any one of the preceding claims, wherein the CoII chelate complex has the formula IV:

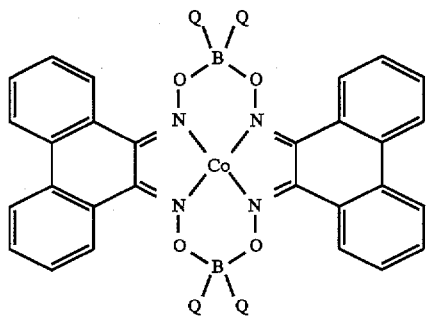

7. Process according to any one of claims 1 to 5, wherein the CoII chelate complex has the formula V:

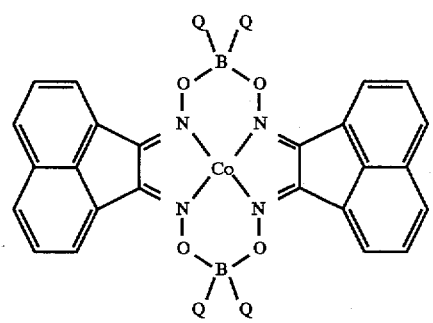

8. Process according to any one of the preceding claims wherein each Q is the same and is selected from F, Cl, Br, OH, $C_{1-12}$ alkyl and $C_{1-12}$ alkoxyl.

9. Process according to claim 8 where each Q is F.

10. Process according to claim 1 wherein said CoII chelate complex has the following formula VI:

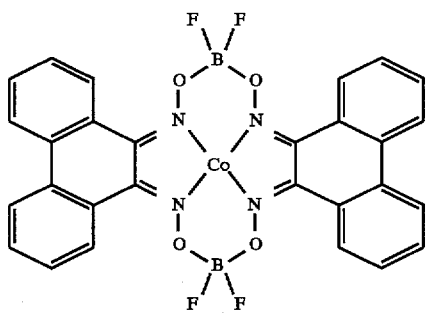

11. Process according to claim 1 wherein said CoII chelate complex has the following formula VII:

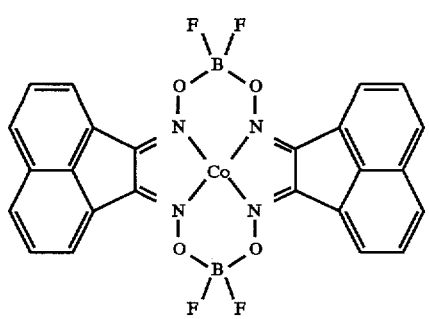

12. Process according to any one of the preceding claims wherein the molecular weight control compound is the CoIII analogue of said CoII chelate in which the Co atom is additionally bonded, in a direction at right angles to the macrocyclic ring system, to H, a halide or other anion, or a homolytically dissociable organic group.

13. Process according to any one of the preceding claims wherein said cobalt chelate has a further ligand(s) coordinated to the cobalt atom which does not alter the cobalt valency state, said ligand being selected from weakly basic tertiary amines, ethers, alkanols, optionally substituted trialkyl, triaryl, or tri(alkyl/aryl)phosphines and the corresponding alkoxy or arloxy phosphines, and water.

14. Process according to any one of the preceding claims wherein said polymerisation is a solution polymerisation in organic solvent.

15. Process according to any one of claims 1 to 13 wherein said polymerisation is an aqueous suspension polymerisation.

16. Process according to any one of the preceding claim wherein said at least one olefinically unsaturated monomer is a methacrylic monomer.

17. Process according to any one of the claim 1 to 15 wherein said process is applied to the homo- or copolymerisation of methacrylate esters or styrenes.

18. Process according to claim 17 wherein the monomer system employed includes an acrylate ester(s).

19. Process according to any one of the preceding claims wherein the monomer system employed includes an acid-functional monomer, preferably being one or both of methacrylic acid and acrylic acid.

20. Process according to any one of claim 1 to 15 wherein said monomer(s) polymerised is selected from at least one of $C_{1-10}$ alkyl methacrylates and acrylates, hydroxy $C_{1-14}$ alkyl methacrylates and acrylates, epoxy $C_{1-14}$ alkyl methacrylates and acrylates, methacrylic acid, acrylic acid, styrene and styrene derivatives.

21. Process according to any one of claims 1 to 15 wherein the monomer polymerised is selected from at least methyl methacrylate, ethyl methacrylate, propyl methacrylate (all isomers), butyl methacrylate (all isomers); the corresponding acrylates; functionalised methacrylates and acrylates selected from glycidyl methacrylate, trimethoxysilyl propyl methacrylate, allyl methacrylate, hydroxyethyl methacrylate, hydroxypropyl methacrylate, dialkylaminoalkyl methacrylates; fluoroalkyl (meth)acrylates; methacrylic acid; acrylic acid; fumaric acid (and esters), itaconic acid (and esters), and maleic anhydride; styrene, α-methyl styrene; vinyl chloride and vinyl fluoride; acrylonitrile, methacrylonitrile; vinylidene halides of formula $CH_2=C(Hal)_2$ where each halogen is independently Cl or F; optionally substituted butadienes of the formula $CH_2=C(R^2)C(R^2)=CH_2$ where $R^2$ is independently H, C1 to C10 alkyl, Cl, or F; sulphonic acids or derivatives thereof of formula $CH_2=CHSO_2OM$ wherein M is Na, K, Li, $N(R^3)_4$, $R^3$, or $—(CH_2)_2—D$ where each $R^3$ is independently H or C1 to C10 alkyl, D is $CO_2Z$, OH, $N(R^3)_2$ or $SO_2OZ$ and Z is H, Li, Na, K or $N(R^3)_4$; acrylamide or derivatives thereof of formula $CH_2=CHSO_2OM$ wherein M is Na, K, Ki, $N(R^3)_4$, $R^3$, or $—(CH_2)_2—D$ where each $R^3$ is independently H or C1 to C10 alkyl, D is $CO_2Z$, OH, $N(R^3)_2$ or $SO_2OZ$ and Z is H, Li, Na, K or $N(R^3)_4$; acrylamide or derivatives thereof of formula $CH_2=CHCON(R^3)_2$, and methacrylamide or derivatives thereof of formula $CH_2=C(CH_3)CON(R^3)_2$, and mixtures of such monomers.

22. An oligomer made using a process according to any one of the preceding claims.

23. An oligomer according to claim 22 wherein said oligomer has a degree of polymerisation of from 2 to 500.

* * * * *